US00RE45790E

(19) United States
(12) Reissued Patent
Figulla et al.

(10) Patent Number: US RE45,790 E
(45) Date of Reissued Patent: Nov. 3, 2015

(54) DEVICE FOR THE IMPLANTATION AND FIXATION OF PROSTHETIC VALVES

(71) Applicant: JenaValve Technology GmbH, München (DE)

(72) Inventors: Hans-Reiner Figulla, Jena (DE); Markus Ferrari, Jena (DE); Christoph Damm, Jena (DE)

(73) Assignee: JENAVALVE TECHNOLOGY GMBH, Munich (DE)

(21) Appl. No.: 14/454,285

(22) Filed: Aug. 7, 2014

Related U.S. Patent Documents

Reissue of:

(64) Patent No.: 8,092,521
Issued: Jan. 10, 2012
Appl. No.: 11/589,570
Filed: Oct. 30, 2006

(30) Foreign Application Priority Data

Oct. 28, 2005 (DE) ..... 10 2005 051 849

(51) Int. Cl.
*A61F 2/24* (2006.01)

(52) U.S. Cl.
CPC ..... *A61F 2/24* (2013.01)

(58) Field of Classification Search
CPC ..... A61F 2/24; A61F 2/2418; A61F 2/2427; A61F 2/243; A61F 2/2436; A61F 2/2439
USPC ..... 623/1.26, 2.38, 2.17, 2.18
See application file for complete search history.

(56) References Cited

U.S. PATENT DOCUMENTS 4,922,905 A 5/1990 Strecker
5,002,566 A 3/1991 Carpentier et al.
5,061,277 A 10/1991 Carpentier et al.
5,094,661 A 3/1992 Levy et al.

(Continued)

FOREIGN PATENT DOCUMENTS

AU 2006308187 A1 5/2007
AU 2006310681 A1 5/2007

(Continued)

OTHER PUBLICATIONS

Aortenklappenbioprothese erfolgreich in der Entwicklung, May 16, 2003 (1 page).

(Continued)

*Primary Examiner* — Catherine S Williams
(74) *Attorney, Agent, or Firm* — Bookoff McAndrews, PLLC

(57) ABSTRACT

A device for the transvascular implantation and fixation of prosthetic heart valves having a self-expanding heart valve stent (10) with a prosthetic heart valve (11) at its proximal end is introducible into a patient's main artery. With the objective of optimizing such a device to the extent that the prosthetic heart valve (11) can be implanted into a patient in a minimally-invasive procedure, to ensure optimal positioning accuracy of the prosthesis (11) in the patient's ventricle, the device includes a self-expanding positioning stent (20) introducible into an aortic valve positioned within a patient. The positioning stent is configured separately from the heart valve stent (10) so that the two stents respectively interact in their expanded states such that the heart valve stent (10) is held by the positioning stent (20) in a position in the patient's aorta relative the heart valve predefinable by the positioning stent (20).

4 Claims, 4 Drawing Sheets

(56) References Cited

U.S. PATENT DOCUMENTS 5,104,407 A 4/1992 Lam et al.
5,197,979 A 3/1993 Quintero et al.
5,279,612 A 1/1994 Eberhardt
5,332,402 A 7/1994 Teitelbaum
5,336,258 A 8/1994 Quintero et al.
5,352,240 A 10/1994 Ross
5,368,608 A 11/1994 Levy et al.
5,411,552 A 5/1995 Andersen et al.
5,456,713 A 10/1995 Chuter
5,509,930 A 4/1996 Love
5,549,666 A 8/1996 Hata et al.
5,595,571 A 1/1997 Jaffe et al.
5,613,982 A 3/1997 Goldstein
5,632,778 A 5/1997 Goldstein
5,674,298 A 10/1997 Levy et al.
5,679,112 A 10/1997 Levy et al.
5,683,451 A 11/1997 Lenker et al.
5,697,972 A 12/1997 Kim et al.
5,713,953 A 2/1998 Vallana et al.
5,746,775 A 5/1998 Levy et al.
5,755,777 A 5/1998 Chuter
5,824,041 A 10/1998 Lenker et al.
5,824,080 A 10/1998 Lamuraglia
5,840,081 A 11/1998 Andersen et al.
5,841,382 A 11/1998 Walden et al.
5,843,181 A 12/1998 Jaffe et al.
5,876,434 A 3/1999 Flomenblit et al.
5,880,242 A 3/1999 Hu et al.
5,895,420 A * 4/1999 Mirsch et al. ..... 623/2.38
5,899,936 A 5/1999 Goldstein
5,928,281 A 7/1999 Huynh et al.
5,935,163 A 8/1999 Gabbay
5,104,407 B1 9/1999 Lam et al.
5,957,949 A 9/1999 Leonhardt et al.
6,001,126 A 12/1999 Nguyen-Thien-Nhon
5,061,277 B1 2/2000 Carpentier et al.
6,077,297 A 6/2000 Robinson et al.
6,093,530 A 7/2000 McIlroy et al.
6,102,944 A 8/2000 Huynh et al.
6,117,169 A 9/2000 Moe
6,126,685 A 10/2000 Lenker et al.
6,168,614 B1 1/2001 Andersen et al.
6,177,514 B1 1/2001 Pathak et al.
6,183,481 B1 2/2001 Lee et al.
6,200,336 B1 3/2001 Pavcnik et al.
6,214,055 B1 4/2001 Simionescu et al.
6,231,602 B1 5/2001 Carpentier et al.
6,254,564 B1 7/2001 Wilk et al.
6,254,636 B1 7/2001 Peredo
6,283,995 B1 9/2001 Moe et al.
6,287,338 B1 9/2001 Sarnowski et al.
6,338,740 B1 1/2002 Carpentier
6,342,070 B1 1/2002 Nguyen-Thien-Nhon
6,344,044 B1 2/2002 Fulkerson et al.
6,350,278 B1 2/2002 Lenker et al.
6,379,740 B1 4/2002 Rinaldi et al.
6,391,538 B1 5/2002 Vyavahare et al.
6,425,916 B1 7/2002 Garrison et al.
6,454,799 B1 9/2002 Schreck
6,471,723 B1 10/2002 Ashworth et al.
6,478,819 B2 11/2002 Moe
6,508,833 B2 1/2003 Pavcnik et al.
6,509,145 B1 1/2003 Torrianni
6,521,179 B1 2/2003 Girardot et al.
6,540,782 B1 4/2003 Snyders
6,558,417 B2 5/2003 Peredo
6,558,418 B2 5/2003 Carpentier et al.
6,572,642 B2 6/2003 Rinaldi et al.
6,582,462 B1 6/2003 Andersen et al.
6,585,766 B1 7/2003 Huynh et al.
6,613,086 B1 9/2003 Moe et al.
6,682,559 B2 1/2004 Myers et al.
6,730,118 B2 5/2004 Spenser et al.
6,736,845 B2 5/2004 Marquez et al.
6,767,362 B2 7/2004 Schreck
6,790,230 B2 9/2004 Beyersdorf et al.
6,808,529 B2 10/2004 Fulkerson
6,821,211 B2 11/2004 Otten et al.
6,821,297 B2 11/2004 Snyders
6,824,970 B2 11/2004 Vyavahare et al.
6,830,584 B1 12/2004 Seguin
6,861,211 B2 3/2005 Levy et al.
6,872,226 B2 3/2005 Cali et al.
6,881,199 B2 4/2005 Wilk et al.
6,893,460 B2 5/2005 Spenser et al.
6,908,481 B2 6/2005 Cribier
6,911,043 B2 6/2005 Myers et al.
6,945,997 B2 9/2005 Huynh et al.
6,974,474 B2 12/2005 Pavcnik et al.
7,014,655 B2 3/2006 Barbarash et al.
7,018,406 B2 3/2006 Seguin et al.
7,037,333 B2 5/2006 Myers et al.
7,050,276 B2 5/2006 Nishiyama
7,078,163 B2 7/2006 Torrianni
7,081,132 B2 7/2006 Cook et al.
7,137,184 B2 11/2006 Schreck
7,141,064 B2 11/2006 Scott et al.
7,163,556 B2 1/2007 Xie et al.
7,189,259 B2 3/2007 Simionescu et al.
7,198,646 B2 4/2007 Figulla et al.
7,201,772 B2 4/2007 Schwammenthal et al.
7,238,200 B2 7/2007 Lee et al.
7,252,682 B2 8/2007 Seguin
7,318,278 B2 1/2008 Zhang et al.
7,318,998 B2 1/2008 Goldstein et al.
7,322,932 B2 1/2008 Xie et al.
7,329,278 B2 2/2008 Seguin et al.
7,381,218 B2 6/2008 Schreck
7,393,360 B2 7/2008 Spenser et al.
7,399,315 B2 7/2008 Iobbi
7,452,371 B2 11/2008 Pavcnik et al.
7,473,275 B2 1/2009 Marquez
7,896,915 B2 3/2011 Guyenot et al.
7,914,575 B2 3/2011 Guyenot et al.
8,398,704 B2 3/2013 Straubinger et al.
8,465,540 B2 6/2013 Straubinger et al.
8,468,667 B2 6/2013 Straubinger et al.
8,551,160 B2 10/2013 Figulla et al.
2001/0011187 A1 8/2001 Pavcnik et al.
2001/0039450 A1 11/2001 Pavcnik et al.
2002/0032481 A1 3/2002 Gabbay
2002/0055775 A1 5/2002 Carpentier et al.
2002/0123790 A1 9/2002 White et al.
2002/0133226 A1 9/2002 Marquez et al.
2002/0151970 A1 10/2002 Garrison et al.
2002/0193871 A1 12/2002 Beyersdorf et al.
2002/0198594 A1 12/2002 Schreck
2003/0014104 A1* 1/2003 Cribier ..... 623/2.11
2003/0023300 A1* 1/2003 Bailey et al. ..... 623/1.13
2003/0027332 A1 2/2003 Lafrance et al.
2003/0036791 A1 2/2003 Philipp et al.
2003/0036795 A1 2/2003 Andersen et al.
2003/0040792 A1 2/2003 Gabbay
2003/0050694 A1 3/2003 Yang et al.
2003/0055495 A1 3/2003 Pease et al.
2003/0065386 A1 4/2003 Weadock
2003/0114913 A1 6/2003 Spenser et al.
2003/0125795 A1 7/2003 Pavcnik et al.
2003/0139796 A1 7/2003 Sequin et al.
2003/0139803 A1 7/2003 Sequin et al.
2003/0149476 A1 8/2003 Damm et al.
2003/0149478 A1 8/2003 Figulla et al.
2003/0153974 A1 8/2003 Spenser et al.
2003/0195620 A1 10/2003 Huynh et al.
2003/0236570 A1 12/2003 Cook et al.
2004/0006380 A1 1/2004 Buck et al.
2004/0039436 A1 2/2004 Spenser et al.
2004/0049262 A1 3/2004 Obermiller et al.
2004/0073289 A1 4/2004 Hartley et al.
2004/0078950 A1 4/2004 Schreck et al.
2004/0102855 A1* 5/2004 Shank ..... 623/23.68
2004/0117004 A1 6/2004 Osborne et al.
2004/0117009 A1 6/2004 Cali et al.
2004/0148018 A1 7/2004 Carpentier et al.

(56) References Cited

U.S. PATENT DOCUMENTS

2004/0153145 A1 8/2004 Simionescu et al.
2004/0186558 A1 9/2004 Pavcnik et al.
2004/0186563 A1 9/2004 Lobbi
2004/0186565 A1 9/2004 Schreck
2004/0193244 A1 9/2004 Hartley et al.
2004/0210301 A1 10/2004 Obermiller et al.
2004/0210304 A1 10/2004 Seguin et al.
2004/0210307 A1 10/2004 Khairkhahan
2004/0260389 A1 12/2004 Case et al.
2005/0009000 A1 1/2005 Wilhelm et al.
2005/0033220 A1 2/2005 Wilk et al.
2005/0033398 A1 2/2005 Seguin
2005/0043790 A1 2/2005 Seguin
2005/0049692 A1 3/2005 Numamoto et al.
2005/0075725 A1 4/2005 Rowe
2005/0075776 A1 4/2005 Cho
2005/0096726 A1 5/2005 Sequin et al.
2005/0096735 A1 5/2005 Hojeibane et al.
2005/0096736 A1 5/2005 Osse et al.
2005/0098547 A1 5/2005 Cali et al.
2005/0113910 A1 5/2005 Paniagua et al.
2005/0119728 A1 6/2005 Sarac
2005/0119736 A1 6/2005 Zilla et al.
2005/0137687 A1 6/2005 Salahieh et al.
2005/0137688 A1 6/2005 Salahieh et al.
2005/0137689 A1* 6/2005 Salahieh et al. ..... 623/2.11
2005/0137690 A1 6/2005 Salahieh et al.
2005/0137697 A1 6/2005 Salahieh et al.
2005/0137698 A1 6/2005 Salahieh et al.
2005/0137702 A1 6/2005 Haug et al.
2005/0143804 A1 6/2005 Haverkost
2005/0143807 A1 6/2005 Pavcnik et al.
2005/0149166 A1 7/2005 Schaeffer et al.
2005/0150775 A1 7/2005 Zhang et al.
2005/0171597 A1 8/2005 Boatman et al.
2005/0171598 A1 8/2005 Schaeffer
2005/0192665 A1 9/2005 Spenser et al.
2005/0197695 A1 9/2005 Stacchino et al.
2005/0222668 A1 10/2005 Schaeffer et al.
2005/0234546 A1* 10/2005 Nugent et al. ..... 623/2.11
2005/0267560 A1 12/2005 Bates
2006/0009842 A1 1/2006 Huynh et al.
2006/0025857 A1 2/2006 Bergheim et al.
2006/0047343 A1 3/2006 Oviatt et al.
2006/0058864 A1 3/2006 Schaeffer et al.
2006/0074484 A1 4/2006 Huber
2006/0074485 A1* 4/2006 Realyvasquez ..... 623/2.11
2006/0111770 A1 5/2006 Pavcnik et al.
2006/0142846 A1 6/2006 Pavcnik et al.
2006/0149360 A1 7/2006 Schwammenthal et al.
2006/0155366 A1 7/2006 LaDuca et al.
2006/0167543 A1 7/2006 Bailey et al.
2006/0178740 A1 8/2006 Stacchino et al.
2006/0193885 A1 8/2006 Neethling et al.
2006/0210597 A1 9/2006 Hiles
2006/0224183 A1 10/2006 Freudenthal
2006/0229718 A1 10/2006 Marquez
2006/0229719 A1 10/2006 Marquez et al.
2006/0246584 A1 11/2006 Covelli
2006/0259134 A1 11/2006 Schwammenthal et al.
2006/0259136 A1 11/2006 Nguyen et al.
2006/0259137 A1 11/2006 Artof et al.
2006/0265056 A1 11/2006 Nguyen et al.
2006/0271161 A1 11/2006 Meyer et al.
2006/0287717 A1 12/2006 Rowe et al.
2006/0287719 A1 12/2006 Rowe et al.
2006/0290027 A1 12/2006 O'Connor et al.
2006/0293745 A1 12/2006 Carpentier et al.
2007/0005129 A1 1/2007 Damm et al.
2007/0005131 A1 1/2007 Taylor
2007/0005132 A1 1/2007 Simionescu et al.
2007/0020248 A1 1/2007 Everaerts et al.
2007/0021826 A1 1/2007 Case et al.
2007/0027535 A1 2/2007 Purdy, Jr. et al.
2007/0032856 A1 2/2007 Limon
2007/0038291 A1 2/2007 Case et al.
2007/0038295 A1 2/2007 Case et al.
2007/0043435 A1 2/2007 Seguin et al.
2007/0050014 A1 3/2007 Johnson
2007/0088431 A1 4/2007 Bourang et al.
2007/0093887 A1 4/2007 Case et al.
2007/0100435 A1 5/2007 Case et al.
2007/0100440 A1 5/2007 Figulla et al.
2007/0112422 A1 5/2007 Dehdashtian
2007/0123700 A1 5/2007 Ueda et al.
2007/0123979 A1 5/2007 Perier et al.
2007/0142906 A1 6/2007 Figulla et al.
2007/0162103 A1 7/2007 Case et al.
2007/0173932 A1 7/2007 Cali et al.
2007/0179592 A1 8/2007 Schaeffer
2007/0185565 A1 8/2007 Schwammenthal et al.
2007/0203576 A1 8/2007 Lee et al.
2007/0213813 A1 9/2007 Von Segesser et al.
2007/0239271 A1 10/2007 Nguyen
2007/0244551 A1 10/2007 Stobie
2007/0260327 A1 11/2007 Case et al.
2007/0288087 A1 12/2007 Fearnot et al.
2008/0004688 A1 1/2008 Spenser et al.
2008/0021546 A1 1/2008 Patz et al.
2008/0033534 A1 2/2008 Cook et al.
2008/0065011 A1 3/2008 Marchand et al.
2008/0071361 A1 3/2008 Tuval et al.
2008/0071362 A1 3/2008 Tuval et al.
2008/0071363 A1 3/2008 Tuval et al.
2008/0071366 A1 3/2008 Tuval et al.
2008/0071368 A1 3/2008 Tuval et al.
2008/0071369 A1 3/2008 Tuval et al.
2008/0077236 A1 3/2008 Letac et al.
2008/0086205 A1 4/2008 Gordy et al.
2008/0097586 A1 4/2008 Pavcnik et al.
2008/0102439 A1 5/2008 Tian et al.
2008/0133003 A1 6/2008 Seguin et al.
2008/0140189 A1 6/2008 Nguyen et al.
2008/0154355 A1 6/2008 Benichou et al.
2008/0200977 A1 8/2008 Paul et al.
2008/0215143 A1 9/2008 Seguin
2008/0255661 A1 10/2008 Straubinger et al.
2008/0262602 A1 10/2008 Wilk et al.
2008/0269878 A1 10/2008 Iobbi
2008/0275549 A1 11/2008 Rowe
2009/0216310 A1 8/2009 Straubinger et al.
2009/0216313 A1 8/2009 Straubinger et al.
2009/0222076 A1 9/2009 Figulla et al.
2009/0234443 A1 9/2009 Ottma et al.
2010/0174362 A1 7/2010 Straubinger et al.
2010/0249915 A1 9/2010 Zhang
2010/0249916 A1 9/2010 Zhang
2010/0249917 A1 9/2010 Zhang
2010/0249918 A1 9/2010 Zhang
2010/0292779 A1 11/2010 Straubinger et al.
2011/0015616 A1 1/2011 Straubinger et al.
2011/0106244 A1 5/2011 Ferrari et al.
2011/0238159 A1 9/2011 Guyenot et al.
2011/0288626 A1 11/2011 Straubinger et al.
2011/0295363 A1 12/2011 Girard et al.
2013/0079869 A1 3/2013 Straubinger et al.
2013/0144203 A1 6/2013 Wilk et al.
2013/0178930 A1 7/2013 Straubinger et al.
2013/0253635 A1 9/2013 Straubinger et al.

FOREIGN PATENT DOCUMENTS

CA 2436258 1/2005
CA 2436258 A1 1/2005
CA 2595233 7/2006
CA 2595233 A1 7/2006
CA 2627555 A1 5/2007
DE 19 546 692 A1 6/1997
DE 20 00 3874 U1 6/2000
DE 19 857 887 A1 7/2000
DE 10 010 073 A1 9/2001
DE 10 010 074 A1 10/2001
DE 10 121 210 A1 11/2002
DE 19 546 692 C2 11/2002

(56) References Cited

FOREIGN PATENT DOCUMENTS

| | | | |
|---|---|---|---|
| DE | 101 21 210 | A1 | 11/2002 |
| DE | 19546692 | C2 | 11/2002 |
| DE | 10 301 026 | A1 | 2/2004 |
| DE | 10335948 | B3 | 7/2004 |
| DE | 10 302 447 | A1 | 2/2005 |
| DE | 10 010 074 | B4 | 4/2005 |
| DE | 19857887 | B4 | 5/2005 |
| DE | 10 010 073 | B4 | 12/2005 |
| DE | 10 2005 051 849 | | 5/2007 |
| DE | 10 2005 052628 | A1 | 5/2007 |
| DE | 20 2007 005 491 | U1 | 7/2007 |
| EP | 0 084 395 | A1 | 7/1983 |
| EP | 0458877 | | 8/1990 |
| EP | 0 402 036 | B1 | 12/1990 |
| EP | 0 402 176 | B1 | 12/1990 |
| EP | 0402176 | B1 | 12/1990 |
| EP | 0 458 877 | B1 | 4/1991 |
| EP | 0 515 324 | A1 | 11/1992 |
| EP | 0 547 135 | B1 | 6/1993 |
| EP | 0871414 | | 9/1995 |
| EP | 0 592 410 | B1 | 10/1995 |
| EP | 0756498 | | 10/1995 |
| EP | 0 592 410 | B1 | 11/1995 |
| EP | 0786970 | | 5/1996 |
| EP | 0 729 364 | B1 | 9/1996 |
| EP | 0 756 498 | B1 | 5/1997 |
| EP | 0 778 775 | B1 | 6/1997 |
| EP | 0786970 | | 8/1997 |
| EP | 0888142 | | 9/1997 |
| EP | 0971649 | | 10/1998 |
| EP | 0 928 615 | A1 | 7/1999 |
| EP | 1051204 | | 7/1999 |
| EP | 1089676 | | 12/1999 |
| EP | 0 986 348 | B1 | 3/2000 |
| EP | 1117446 | | 4/2000 |
| EP | 1 164 976 | | 8/2000 |
| EP | 1158937 | | 9/2000 |
| EP | 1 041 942 | B1 | 10/2000 |
| EP | 1 041 943 | B1 | 10/2000 |
| EP | 1171061 | | 10/2000 |
| EP | 1206179 | | 2/2001 |
| EP | 1 117 446 | B1 | 7/2001 |
| EP | 1 255 510 | | 8/2001 |
| EP | 1259193 | | 9/2001 |
| EP | 1 206 179 | B1 | 5/2002 |
| EP | 1347785 | | 8/2002 |
| EP | 1235537 | | 9/2002 |
| EP | 1 251 804 | B1 | 10/2002 |
| EP | 1248655 | | 10/2002 |
| EP | 1251804 | B1 | 10/2002 |
| EP | 1257305 | | 11/2002 |
| EP | 0 971 649 | B1 | 12/2002 |
| EP | 1395208 | | 12/2002 |
| EP | 1 401 359 | | 1/2003 |
| EP | 1406561 | | 1/2003 |
| EP | 1 281 375 | A2 | 2/2003 |
| EP | 1281357 | A2 | 2/2003 |
| EP | 1281375 | A2 | 2/2003 |
| EP | 1408882 | | 2/2003 |
| EP | 1 435 878 | | 4/2003 |
| EP | 1 435 879 | | 4/2003 |
| EP | 1 441 672 | | 6/2003 |
| EP | 1 017 868 | B1 | 9/2003 |
| EP | 1354569 | A1 | 10/2003 |
| EP | 1494616 | | 10/2003 |
| EP | 1 519 697 | | 1/2004 |
| EP | 1 539 047 | | 4/2004 |
| EP | 1551274 | | 4/2004 |
| EP | 1 560 542 | | 5/2004 |
| EP | 1414295 | | 5/2004 |
| EP | 1 452 153 | A1 | 9/2004 |
| EP | 1 603 493 | | 9/2004 |
| EP | 1452153 | A1 | 9/2004 |
| EP | 0 987 998 | B1 | 10/2004 |
| EP | 1 087 727 | B1 | 11/2004 |
| EP | 1 233 731 | B1 | 12/2004 |
| EP | 1 499 366 | B1 | 1/2005 |
| EP | 1 663 070 | | 3/2005 |
| EP | 1 253 875 | B1 | 4/2005 |
| EP | 1 667 614 | | 4/2005 |
| EP | 1 251 803 | B1 | 6/2005 |
| EP | 1 702 247 | | 7/2005 |
| EP | 1734902 | | 8/2005 |
| EP | 1 469 797 | B1 | 11/2005 |
| EP | 1835948 | | 6/2006 |
| EP | 1 690 515 | A1 | 8/2006 |
| EP | 1863545 | | 9/2006 |
| EP | 1893132 | | 11/2006 |
| EP | 1901681 | | 12/2006 |
| EP | 1 251 805 | B1 | 3/2007 |
| EP | 1 255 510 | B1 | 3/2007 |
| EP | 1835948 | | 9/2007 |
| EP | 1 112 042 | B1 | 11/2007 |
| EP | 1 878 407 | A1 | 1/2008 |
| EP | 1 886 649 | A2 | 2/2008 |
| EP | 1 900 343 | A2 | 3/2008 |
| EP | 1 259 195 | B1 | 10/2008 |
| EP | 1 980 220 | A1 | 10/2008 |
| EP | 1259195 | B1 | 10/2008 |
| EP | 1 99 4913 | A2 | 11/2008 |
| EP | 2 000 115 | A2 | 12/2008 |
| FR | 2 828 263 | A1 | 2/2003 |
| GB | 2433700 | A | 7/2007 |
| GB | 2440809 | A | 2/2008 |
| JP | 2003-523262 | | 8/2003 |
| JP | 2003-524504 | | 8/2003 |
| JP | 2005-118585 | | 5/2005 |
| JP | 2007-296375 | | 11/2007 |
| WO | WO 90/09102 | | 8/1990 |
| WO | WO 95/11055 | A1 | 4/1995 |
| WO | WO 95/24873 | | 9/1995 |
| WO | WO 95/28183 | | 10/1995 |
| WO | WO 96/13227 | | 5/1996 |
| WO | WO 97/32615 | | 9/1997 |
| WO | WO 98/43556 | | 10/1998 |
| WO | WO 98/46165 | | 10/1998 |
| WO | WO 99/37337 | | 7/1999 |
| WO | WO-99/66863 | | 12/1999 |
| WO | WO 00/15148 | | 3/2000 |
| WO | WO 00/18445 | | 4/2000 |
| WO | WO 00/25702 | A1 | 5/2000 |
| WO | WO 00/47139 | A1 | 8/2000 |
| WO | WO 00/53125 | | 9/2000 |
| WO | WO 00/62714 | | 10/2000 |
| WO | WO 01/10209 | A1 | 2/2001 |
| WO | WO 01/35870 | A1 | 5/2001 |
| WO | WO 01/41679 | A1 | 6/2001 |
| WO | WO 01/51104 | A1 | 7/2001 |
| WO | WO 01/54625 | A1 | 8/2001 |
| WO | WO 01/58503 | A1 | 8/2001 |
| WO | WO 01/62189 | A1 | 8/2001 |
| WO | WO 01/64137 | A1 | 9/2001 |
| WO | WO 02/36048 | A1 | 5/2002 |
| WO | WO 02/058745 | A1 | 8/2002 |
| WO | WO 02/100301 | A1 | 12/2002 |
| WO | WO 02/102286 | A1 | 12/2002 |
| WO | WO 03/003949 | A2 | 1/2003 |
| WO | WO 03/007795 | A2 | 1/2003 |
| WO | WO 03/009785 | A1 | 2/2003 |
| WO | WO 03/011195 | A2 | 2/2003 |
| WO | WO 03/013239 | | 2/2003 |
| WO | WO 03/028592 | A1 | 4/2003 |
| WO | WO 03/047468 | A1 | 6/2003 |
| WO | WO 03/079928 | A2 | 10/2003 |
| WO | WO 03/096935 | A1 | 11/2003 |
| WO | WO 2004/004597 | A2 | 1/2004 |
| WO | WO 2004/016200 | A1 | 2/2004 |
| WO | WO 2004/016201 | A2 | 2/2004 |
| WO | WO 2004/019825 | A1 | 3/2004 |
| WO | WO 2004/026117 | A2 | 4/2004 |
| WO | WO 2004/026173 | A2 | 4/2004 |
| WO | WO 2004/028399 | A2 | 4/2004 |
| WO | WO 2004/043301 | A1 | 5/2004 |
| WO | WO 2004/082527 | A2 | 9/2004 |

(56) References Cited

FOREIGN PATENT DOCUMENTS

| | | | |
|---|---|---|---|
| WO | WO 2004/082528 | A2 | 9/2004 |
| WO | WO 2004/096100 | A1 | 11/2004 |
| WO | WO 2005/021063 | A2 | 3/2005 |
| WO | WO 2005/034812 | A1 | 4/2005 |
| WO | WO 2005/062980 | A | 7/2005 |
| WO | WO 2005/062980 | A2 | 7/2005 |
| WO | WO 2005/063980 | A1 | 7/2005 |
| WO | WO 2005/070343 | A1 | 8/2005 |
| WO | WO 2005/072654 | A1 | 8/2005 |
| WO | WO 2006/066327 | A1 | 6/2006 |
| WO | WO 2006/076890 | A1 | 7/2006 |
| WO | WO 2006/102063 | A2 | 9/2006 |
| WO | WO 2006/108090 | A2 | 10/2006 |
| WO | WO 2006/124649 | A2 | 11/2006 |
| WO | WO 2006/127756 | A2 | 11/2006 |
| WO | WO 2006/127765 | A1 | 11/2006 |
| WO | WO 2006/132948 | A1 | 12/2006 |
| WO | WO 2007/047488 | A2 | 4/2007 |
| WO | WO 2007/047945 | A2 | 4/2007 |
| WO | WO 2007/051620 | A1 | 5/2007 |
| WO | WO 2007/059252 | A1 | 5/2007 |
| WO | WO 2007/071436 | A2 | 6/2007 |
| WO | WO 2007/098232 | A2 | 8/2007 |
| WO | WO 2007/120543 | A1 | 10/2007 |
| WO | WO 2008/028569 | A1 | 3/2008 |
| WO | WO 2008/035337 | A | 3/2008 |
| WO | WO 2008/045949 | | 4/2008 |
| WO | WO 2008/070797 | A2 | 6/2008 |
| WO | WO 2006/076890 | | 7/2008 |
| WO | WO 2008/079962 | A1 | 7/2008 |
| WO | WO 2008/101083 | A2 | 8/2008 |
| WO | WO 2008/125153 | A1 | 10/2008 |
| WO | WO 2008/138584 | A1 | 11/2008 |
| WO | WO 2008/150529 | A | 12/2008 |

OTHER PUBLICATIONS

English translation of Aortenklappenbioprotheseerfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," *Eur. J. Cardio-Thoracic Surgery*, vol. 28, pp. 194-198 (2005) (5 pages).
Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).
English translation of DE 19 546 692 A1 (4 pages).
English translation of EP 1 469 797 B1 (16 pages).
International Search Report for PCT/EP2006/010023.
Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).
Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).
File history for Geman Patent DE 195 46 692 filed Dec. 14, 1995 and patented Jul. 11, 2002.
International Search Report for PCT/EP2006/010023, Mar. 23, 2007.
Aortenklappenbioprothese erfolgreich in der Entwicklung, (1 page) May 16, 2003.
Translation of Aortenklappenbioprothese erfolgreich in der Entwicklung ( 2 pages).
Screen shots from http://www.fraunhofer.de/presse/filme/2006/index.jsp (2 pages), 2006.
Liang, Ma, et al., "Double-crowned valved stents for off-pump mitral valve replacement," European Journal of Cardio-Thoracic Surgery, 194-198 (5 pages), Jun. 13, 2005.
Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.
Translation of DE 19546692 A1 (4 pages), Jun. 19, 1997.
Translation of EP 1469797 B1 (16 pages), Feb. 11, 2005.

* cited by examiner

DEVICE FOR THE IMPLANTATION AND FIXATION OF PROSTHETIC VALVES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The present invention relates to a device for the transvascular implantation and fixation of prosthetic heart valves having a self-expanding heart valve stent with a prosthetic heart valve at its proximal end.

2. Background Information

A device of this type is, in principle, known to medical technology. At present, biological or mechanical valve models are available to substitute for human heart valves which are usually fixedly sewn into the bed of the heart valve during a surgical procedure through an opening in the chest after removal of the diseased heart valve. In this surgical procedure, the patient's circulation must be maintained by a heart-lung machine, whereby cardiac arrest is induced during the implantation of the prosthetic heart valve. This consequently makes the surgical procedure a risky one coupled with the associated risks for the patients and a lengthy post-operative treatment phase. In particular, such a procedure cannot be performed on patients whose hearts are already too weak.

Minimally-invasive treatment procedures of recent development are characterized in particular by requiting a considerably shortened duration of anesthesia. One approach provides for implanting a self-expanding prosthetic heart valve with an artificial heart valve and a collapsible and expandable stent connected to the heart valve into the human body by means of an appropriate catheter system. The catheter system is used to guide such a self-expanding prosthetic heart valve through a femoral artery or vein to its site of implantation at the heart. After reaching the site of implantation, the stent, which consists for example of a plurality of self-expanding stent segments which can be bent relative one another in the longitudinal direction, can then be successively expanded. Following the expansion, anchoring hooks can for example support the anchoring of the prosthetic heart valve at least in the respective blood vessel close to the heart. The actual prosthetic heart valve itself is thereby in the direct proximal area of the stent.

Known for example from the DE 100 10 074 AI printed publication is a device for fastening and anchoring prosthetic heart valves, which is essentially formed from wire-shaped interconnected elements. The device provides for using various different arched elements in order to attain a secure retention and support for the prosthetic heart valve. To this end, the device described in this printed publication makes use of three identical pairs of arched elements, offset from one another by 120°. These arched elements are interconnected by means of solid articulations, whereby the solid articulations fulfill the function of pivot bearings. Additional arched elements bent opposite to each other are furthermore provided which form rocker arms as equal in length as possible in order to achieve a secure anchoring of the arched elements even when subject to peristaltic actions on the heart and blood vessels and a solid sealing for an implanted and anchored prosthetic heart valve.

In the known solutions, however, there is a risk of heart valve implant malalignment. This essentially refers to the exact positioning and angular adjustment of the prosthetic heart valve to be implanted. In particular, it is only with immense skill on the part of the person performing the implantation—if at all—that a stent with the prosthetic heart valve at its proximal end winds up being positioned so precisely in the proximity of the patient's diseased heart valve that both sufficient lateral positioning accuracy as well as a suitable angular position to the prosthetic heart valve can be optimally ensured. The known solutions are also only conditionally suitable for explanting improperly or incorrectly positioned prosthetic heart valves. Such a process is usually only possible with great effort; in particular, a further surgical procedure is required.

Among other complications, an implantation malalignment of a less than optimally positioned prosthetic heart valve can lead to, for example, leakage or valvular regurgitation, which puts a substantial burden on the ventricle. Should, for example, a prosthetic heart valve be implanted too high above the actual heart valve plane, this can lead to occlusion of the coronary artery origination (coronaries) and thus to a fatal coronary ischemia with myocardiac infarction. It is therefore imperative for an implanted prosthetic heart valve to meet all the respective requirements for both the accuracy of the lateral positioning as well as the angular positioning.

In conventional implantation techniques in which self-expanding prosthetic heart valves are, for example, guided through a patient's femoral artery to the site of deployment at the heart in a minimally-invasive procedure, the prosthesis is usually introduced using a guide wire and catheters, whereby conventional balloon catheters can also be used. Although such a surgical introduction can be monitored and controlled, for example with fluoroscopy (Cardiac Catheterization Laboratory=CCL) or with ultrasound (Trans-esophageal Echocardiogram=TEE), oftentimes—due to the limited maneuverability of the prosthetic heart valve which is still in a collapsed state during the introduction procedure and despite being in the collapsed state is still of relatively large size—it is not possible to ensure the required positioning accuracy and especially the angular position to the prosthetic heart valve implant with the corresponding anchoring elements affixed thereto. In particular—as a result of a possible coronary artery occlusion—an anglular misalignment to the implanted prosthetic heart valve from the optimum site of deployment can pose a threat to the respective patient.

In designing a prosthetic heart valve, special consideration must, in particular, be given to the substantial forces also acting on the prosthesis during the filling period of the cardiac cycle (diastole), necessitating a secure anchorage in order to prevent the implanted prosthetic heart valve from dislodging.

Hence on the one hand, the prosthetic heart valve must be able to be maneuvered as much as possible in the respective coronary artery during the implantation procedure so as to ensure optimum positioning accuracy and, on the other hand, the implanted prosthesis must be able to be firmly anchored at its site of implantation in order to effectively prevent subsequent prosthesis misalignment.

The present invention addresses the problem that the known devices for transvascular implantation and fixation of prosthetic heart valves are often not suitable for easily implanting a prosthetic heart valve in a patient's ventricle with the necessary positioning accuracy. In particular, the necessary lateral positioning accuracy and the angular position of the prosthetic heart valve can usually only be sufficiently guaranteed when the person performing the procedure has the corresponding experience. On the other hand, explanting a previously implanted prosthetic heart valve in a minimally-invasive procedure or accordingly correcting an incorrectly positioned prosthetic heart valve has to date is only been possible with great effort, if at all.

On the basis of this problem as set forth, the present invention proposes a device which enables a prosthetic heart valve to be implanted into a patient in a minimally-invasive procedure in as simple a manner as possible, wherein an increased positioning accuracy to the prosthesis in the patient's ventricle can in particular be ensured. Such a device is to, in particular, reduce the risk of an incorrect deployment to the greatest extent possible.

SUMMARY OF THE INVENTION

According to the invention, this task is solved by a device as described at the outset by the device having, in addition to the self-expanding heart valve stent with a prosthetic heart valve at its proximal end, a self-expanding positioning stent insertable into a position in the patient's aortic valve, which is configured separate from the heart valve stent, wherein the positioning stent and the heart valve stent are configured such that they each work in concert in their expanded states so that the positioning stent helps to hold the heart valve stent in a position relative the patient's heart valve predefined by the positioning stent.

The device according to the invention exhibits an entire array of substantial advantages over the prosthetic heart valves known from the prior art and described above. The two-part configuration of the device in the design of the heart valve stent and the positioning stent configured separately therefrom can, in particular, greatly increase the positioning accuracy of the prosthetic heart valve in the patient's ventricle. The positioning stent hereby primarily assumes the function of determining the position of the prosthetic heart valve in the patient's ventricle as well as the function of anchoring or fixing the prosthesis at optimum placement. In particular, the prosthetic heart valve is not on or in the positioning stent, but instead configured separately from the positioning stent on the heart valve stent This has the advantage that the dimensions of the positioning stent in its collapsed state are extremely small, which increases the stent's maneuverability.

The heart valve stent primarily serves the inventive device only as a supporting structure for the prosthetic heart valve to be implanted. This function sharing enables both the positioning stent as well as the heart valve stent to be of relatively simple configuration. What can be achieved in particular is that compared to a stent on which both a prosthetic heart valve as well as means for positioning and fixing the prosthetic heart valve are arranged, the positioning stent can be configured to exhibit only relatively small dimensions in its collapsed state. Inserting the positioning stent in the patient's artery is thus—due to the better maneuverability achieved—substantially simpler. A direct consequence of this is increased positioning accuracy for the positioning stent.

The device according to the invention is configured in such a manner that not until the positioning stent is positioned into the patient's artery and after aligning the stent with respect to a predefinable axial rotation and horizontal position relative an (old) heart valve of the patient is the heart valve stent configured separately from the positioning stent inserted into the artery or vein. During the insertion procedure, the heart valve stent, which has the prosthetic heart valve at its proximal end, independently orientates itself to the exactly-positioned positioning stent as fixed at the arterial wall. Specifically, the heart valve stent is independently guided within the expanded positioning stent into the implantation position predefined by the positioning stent at which the prosthetic heart valve is in an optimum position relative the patient's old heart valve. After the heart valve stent, aided by the positioning stent, has positioned into the coronary artery in the predefined position relative the old heart valve, the full expansion of the heart valve stent is induced, for example by an external manipulation, as a consequence of which the heart valve stent according to the invention interacts with the positioning stent in such a way that the heart valve stent, and thus also the prosthetic heart valve disposed at its proximal end, is positionally fixed into the implantation position. Accordingly, the positioning stent serves—in addition to the already mentioned function of defining the position for the prosthetic heart valve in the patient's ventricle and the function of anchoring or fixing the prosthesis at this position—also the function of guiding the heart valve stent into the optimum position for the prosthetic heart valve during the implantation procedure. The advantages attainable with the inventive device are obvious: in particular, an optimum positioning is enabled for the prosthetic heart valve in its final implanted position, whereby the alignment and fixing of the prosthetic heart valve ensues independently based on the co-operative action of the heart valve stent and the positioning stent. On the one hand, a position-contingent, inaccurate implantation of the prosthetic heart valve can hereby be excluded. On the other hand, the device is characterized by the implantation and anchoring of the prosthetic heart valve ensuing in a particularly simple manner.

Because the positioning stent according to the invention is configured to be an insertable, self-expanding component in a patient's blood vessel, it can be inserted beforehand; i.e., prior to the actual implantation of the prosthetic heart valve disposed at the proximal end of the heart valve stent. It would thus be conceivable here for the positioning stent to first be brought into the aorta and optimally positioned and fixed there, whereby the heart valve stent with the prosthetic heart valve is thereafter introduced and inserted optimally by means of the positioning stent already in position and fixed there.

According to the invention, both the heart valve stent as well as the positioning stent are configured to self-expand, which facilitates the respective introduction of these components. Because the positioning stent assuming the task of determining the position for the heart valve stent, the prosthetic heart valve disposed thereon respectively, can be configured to be substantially smaller in comparison to previous self-expanding prosthetic heart valves, the maneuverability of the positioning stent is increased considerably, which ultimately results in being able to select an extremely precise position at which the positioning stent is anchored relative the heart valve and one ideally adapted to the respective requirements. This advantage of exact positioning of the easily-maneuvered and minutely-configured positioning stent extends to the subsequent implantation of the prosthetic heart valve since the heart valve stent, at the proximal end of which the prosthetic heart valve is arranged, is held in the position defined by the (optimally positioned) positioning stent.

Advantageous further developments of the inventive device are specified in the dependent claims.

One particularly advantageous development with respect to insertion of the heart valve stent provides for the heart valve stent to be configured to be reversibly expandable and collapsible. It is thereby conceivable for the heart valve stent to be collapsed, for example via external manipulation, and extracted using an explantation catheter. Specifically, this embodiment enables the heart valve stent in collapsed form to be connectably received in a cartridge of a positioning catheter, an explantation catheter respectively. In order for the heart valve stent to be optimally inserted into a patient's blood vessel and positioned there in a predefined position relative the heart valve, it is necessary for the positioning stent to be as small as possible in its collapsed state so that the stent can be optimally navigated with as little impact as possible on the heart valve. This is achieved by the prosthetic heart valve implant not being affixed to the positioning stent but rather to the heart valve stent. The positioning stent is furthermore configured such that all the components of the stent in the collapsed state have a certain measure of pretensioning acting in a radially outward direction which effects the self-expansion following release from the cartridge. The positioning stent can then be implanted with the cartridge in conventional manner using a positioning stent catheter, for example through a femoral artery. Should the positioning stent be inaccurately deployed, for example if the positioning stent is not positioned precisely accurately in the patient's aorta, or when an explantation of the positioning stent is necessary for other reasons, it is provided for the positioning stent to be convertible from its expanded state back into its collapsed state. This is done for example by external manipulation using an implantation catheter. The positioning stent is thus fully reversibly withdrawable in the catheter, which enables the stent to be completely removed.

The inventive device for transvascular implantation and fixation of prosthetic heart valves can advantageously provide for the positioning stent to have an anchorage at its proximal end, in particular an anchoring support, whereby this anchoring support is configured such that the positioning stent self-positions into a pre-defined position relative the patient's heart valve in its expanded state and is held by means of the anchoring support. The positioning stent is thereby configured such that the anchoring support is received in collapsed form in a cartridge connectable with a catheter. The anchoring support is thereby to be compressed such that it is pretensioned in a radially outward direction which effects the self-expansion following release from the cartridge. Configuring the positioning stent so that it self-positions into a given position relative the patient's heart valve in its expanded state and is held there by means of the anchoring support enables the position of the positioning stent and thus the position of the heart valve stent to be precisely definable beforehand so that inaccurate implantations, as can occur with the known solutions, can be excluded.

In order to facilitate the positioning stent's self-expansion, the positioning stent can advantageously furthermore exhibit pretensioning elements in order to radially pretension the positioning stent in its position defined by the anchorage. The pretensioning elements are thereby also configured to be reversible so that their pretensioning function can be countermanded by external manipulation, which enables the positioning stent to be collapsed and thus be retracted into a catheter, enabling the positioning stent to be removed completely.

An advantageous realization of the latter embodiment provides for the anchoring support to have at least one support strut which is configured such that it self-positions into the pockets of the patient's heart valve in the expanded state of the positioning stent and thus fixes the orientation of the positioning stent relative the heart valve in the axial and horizontal direction. Hereby conceivable would be, for example, that the support struts configured at the proximal end of the positioning stent implant independently in the pockets of the respective patient's heart valve during the implantation procedure, whereby the pockets of the heart valve form a counter bearing for counteracting the proximal insertion motion so that the anchoring supports can be precisely positioned laterally with the positioning stent. Since the pockets represent a guide per se for the support struts during insertion, this ensures at the same time that the anchoring support and the positioning stent can adopt a precise angular position. Only after the support struts have been introduced into the pockets of the respective patient's heart valve and the final position for the positioning stent has been reached is the heart valve stent configured separately from the positioning stent deployed with the help of, for example, a heart valve catheter. The heart valve stent exhibiting the prosthetic heart valve at its proximal end is then optimally implanted at the most favorable and ideal site by means of the positioning stent already having been exactly positioned and fixed. To be mentioned as a further advantage is that the support struts of the positioning stent are positioned at the patient's heart valve following implantation of the positioning stent. Because the positioning stent is of relatively simple configuration, since it for example does not comprise the prosthetic heart valve which is disposed separately from the positioning stent on the heart valve stent, the struts of the positioning stent can exhibit a relatively large radius, which entails a lesser risk of injury to the heart valve.

The support strut disposed on an anchoring support or anchorage should be curved convexly and arcuately in the proximal direction because such a rounded form wards off injuries to the heart's blood vessel as well as facilitates the unfolding in the self-expansion process. With such a design, inserting the support struts into the pockets of the old heart valve is thus likewise easier without engendering any corresponding injuries to the tissue or the blood vessels of the region.

Additional stabilizing struts can also be provided on the anchoring supports, which achieves increased fixedness following the self-expansion of the anchored anchoring supports. Such stabilizing struts can be advantageous since in order to benefit from the self-expansion effect required of an anchoring support for securely fixing the anchoring support with the positioning stent, accepting that the anchoring supports collapsed within a cartridge during the introduction phase must be of the smallest volume possible, small cross-sections for the respective struts must be maintained.

All the struts of an anchoring support should thereby be arranged, configured and dimensioned such that the successively ensuing release of the supporting struts and the other struts with the further elements provided on an anchoring support, as the case may be, can be achieved by the appropriate manipulation of cartridge and/or catheter. In so doing, the design of the cartridge or at least a portion of the cartridge should, of course, also be taken into consideration.

Corresponding to physical anatomy, three supporting struts each arranged at the same angular spacing from one another on the anchoring support should be provided. Yet there is also the possibility of arranging each of the supporting struts disposed on an anchoring support to be at an angular offset from one another. In this case, the supporting struts with their proximal members are then introduced into the pockets of an old heart valve in the implanted state and the old heart valve can then be tightly secured and fixed with the supporting struts.

The stability of an implanted and fixed positioning stent can be optimally increased by means of at least one ring support, which can be an element on an anchoring support. Thus, by means of such a ring support, the possibility exists of connecting different struts provided on an anchoring support, preferably at their bases. It is thereby not imperative to provide a connection between the ring support and all the struts of an anchoring support.

After the positioning stent is positioned at the heart and held there by the anchorage, the heart valve stent is introduced. It is hereby advantageously provided for the heart valve stent to be configured such that the prosthetic heart valve in its expanded state presses the patient's heart valve against the aorta wall, whereby the at least one anchorage of the positioning stent positions between the aorta wall and the heart valve expanded by the prosthetic heart valve.

In order to have the heart valve stent be held in a position defined by the positioning stent relative the patient's heart valve using the positioning stent, the positioning stent has at least one engaging element at its distal end. The heart valve stent should thereby exhibit a correspondingly complementary-configured retaining element at its distal end, whereby in the expanded state of the positioning stent and in the fully expanded state of the heart valve stent, the at least one retaining element forms a positive connection with the at least one engaging element of the positioning stent. This thus achieves the positioning of the prosthetic heart valve in the coronary artery in the position predefined by the positioning stent and it being held there by the positioning stent. It would hereby be conceivable to provide engaging clips on the heart valve stent. The engaging clips are thereby among the elements of the heart valve stent which are not released to expand until the heart valve stent is accurately inserted into its implantation deployment site at the patient's heart valve by means of the already implanted positioning stent. When the engaging clips of the heart valve stent expand, they engage with the engaging elements of the positioning stent and thus hold the heart valve stent in the position given by the positioning stent. At the same time, portions of the respective patient's old heart valve then each work into an anchoring strut of the positioning stent and the expanded prosthetic heart valve so that the respective portions of the old heart valve can be clamped and held between these elements following the successful expanding of the prosthetic heart valve, similar to how a sheet of paper is held between the brackets of a paper clip.

The heart valve stent is in particular configured such that it does not adopt its fully expanded state, in which both the prosthetic heart valve as well as also the retaining element is released, until the heart valve stent is in the position as defined by the positioning stent.

As is the case with the positioning stent, the heart valve stent is also advantageously configured to be reversible in its folding action, whereby the positive connection with the positioning stent is disengaged in the collapsed state. This thus allows the prosthetic heart valve disposed on the heart valve stent to again be explanted, for example in the case of an improper implantation, without also having to extract the positioning stent in order to do so.

In order to facilitate explantation of the heart valve stent, explantation elements can be provided at the distal end of the heart valve stent which work in concert with the heart valve stent such that when externally manipulated, for example, the explantation elements disengage the positive connection between the heart valve stent and the positioning stent, and the heart valve stent collapses. One advantageous realization of the explantation elements provides for their being engageable, for example by means of an explantation catheter, whereby retracting the explantation elements in the explantation catheter disengages the positive connection between the heart valve stent and the positioning stent, and the heart valve stent folds back up.

The heart valve stent is advantageously accommodated in the collapsed state in a cartridge connectable to a heart valve stent catheter and/or explantation catheter, whereby a predefinable motion of the cartridge will release the heart valve stent. Specifically, it is thereby advantageously provided that a predefinable first motion of the cartridge will only release the prosthetic heart valve to expand, whereby the retaining element of the heart valve stent is released by at least one second subsequent motion of the cartridge, the catheter respectively.

It can be advantageous, in particular for the subsequent cartridge and catheter movement, which leads to the sequential release of the individual elements of the heart valve stent, to use a multi-part cartridge, whereby at least two individual parts can each be moved relative one another. Hence, the movements of a cartridge or individual parts of a cartridge to be realized, for example so as to lead to self-expansion, can be a proximal and/or distal displacement, which can ensue in several successive stages, each covering different paths in order to successively release the corresponding parts for their respective expansion during implantation.

Thus, a first movement, for example, can be a distal retraction of the cartridge or a portion of a cartridge. Should it hereby be necessary so as to avoid inaccurate implantation, a proximal movement of the cartridge or a portion of a cartridge can then be effected to re-collapse the already-expanded retaining elements acting radially outwardly with a pretensioning force, the prosthetic heart valve of the heart valve stent respectively, and to bring same into the interior of the cartridge so as to enable the device to be removed from the patient. Bowden cables or flexible push tubes guided through the interior of the catheter to the cartridge or to a portion of the cartridge can be used as the actuating elements for a manipulation and the associated displacing movement of the cartridge or individual parts of the cartridge. Such actuating elements can, however, also engage with fastening elements, for example eyelets, provided on the anchoring support.

The solution according to the invention thus also provides the possibility of aborting prosthetic heart valve implantations which will be unsuccessful and removing the device again by withdrawing the catheter, whereby in so doing, the heart valve stent which has already expanded re-collapses again and can be guided back into a cartridge or a portion of a cartridge.

An advantageous further development of the device according to the invention provides for the positioning stent to furthermore comprise anchoring elements, in particular hooks, in order to anchor the positioning stent in its predefinable position at the heart. Additionally or alternatively to the positioning stent, it would be conceivable for the heart valve stent to also comprise anchoring elements such as hooks, for example, in order to anchor the heart valve stent in the position in the aorta as predefined by the positioning stent. Both solutions ultimately serve the secure fixing of the implanted prosthetic heart valve at its site of implantation as predefined by the positioning stent.

In order to facilitate spatial orientation when inserting the positioning stent, markers can be disposed on the positioning stent, in particular x-ray markers. Of course, other solutions are also conceivable. For example, insertion of the positioning stent can also be monitored and controlled using fluoroscopy (Cardiac Catheterization Laboratory=CCL) or ultrasound (Transesophageal Echocardiogram=TEE).

The positioning stent and/or the heart valve stent can furthermore exhibit guiding means which are configured in such a manner that the heart valve stent is guided independently in the expanded positioning stent into the position predefined by the positioning stent. It would hereby be conceivable for the guiding means to be configured as elements tapering to the distal end of the positioning stent, the heart valve stent respectively, so as to realize a self-adjusting of the heart valve stent in the positioning stent and thus into the position predefined by the positioning stent.

The device according to the invention can also be used together with a balloon catheter. With a balloon catheter, the old heart valve can be pushed away prior to the self-expansion of the anchoring support.

The following will make reference to the figures in describing preferred embodiments of the device according to the invention for the implantation and fixation of prosthetic heart valves in greater detail.

DETAILED DESCRIPTION OF AN ILLUSTRATIVE EMBODIMENT

Figure 1:
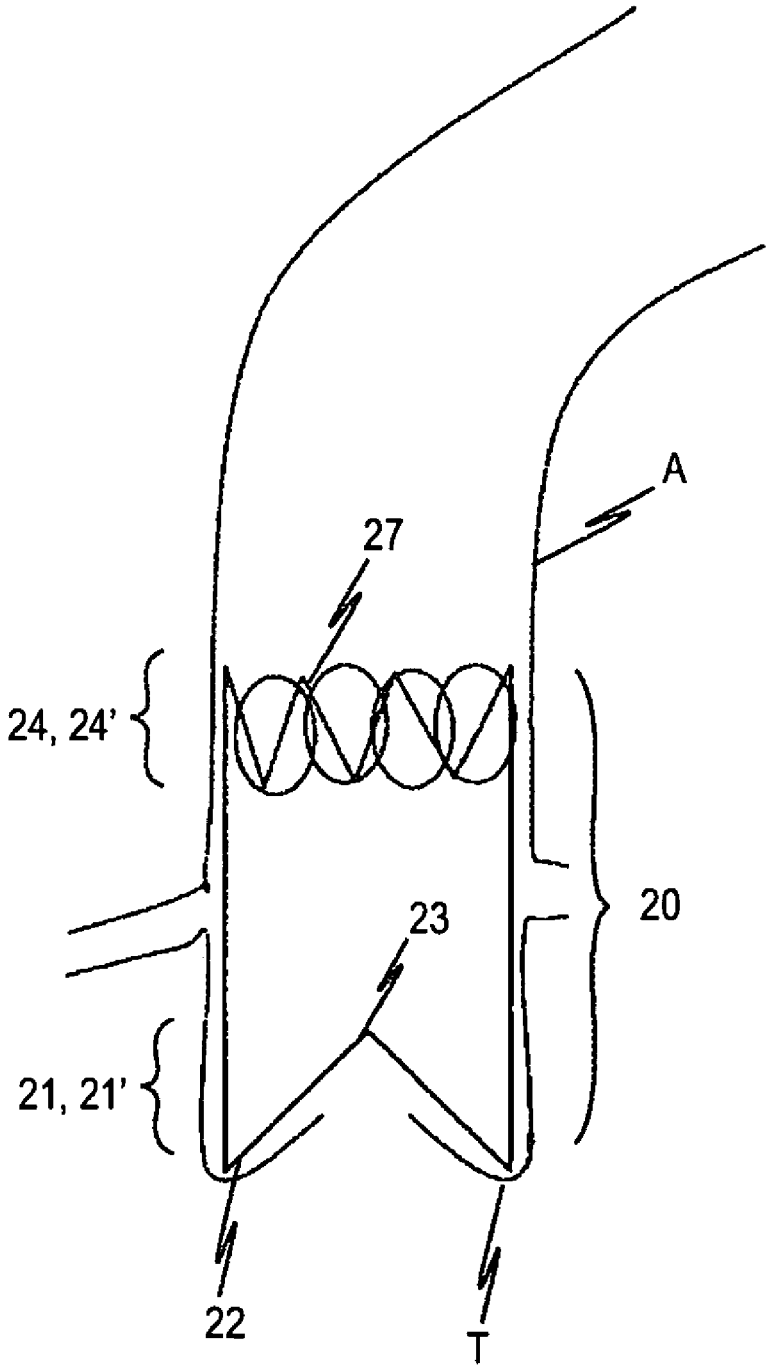
FIG. 1: a preferred embodiment of a positioning stent of the device according to the invention in the inserted and expanded state.

FIG. 1 shows a preferred embodiment of a positioning stent 20 for the device according to the invention in the inserted state. The positioning stent 20 is in its expanded state in the embodiment shown. As depicted, the positioning stent 20 has an anchoring segment 21' with anchoring supports 21 at its proximal end. The anchoring supports 21 are hereby configured such that they optimize themselves into the pockets T of the old heart valve relative to axial rotation as well as horizontal position. To this end, the positioning stent 20 is supported by means of anchoring supports 21 in pockets T of the old heart valve. The anchoring supports 21 themselves are connected to docking segment 23 by means of shoulders 22. The docking segment 24' of positioning stent 20, provided at its distal end, exhibits a plurality of engaging elements 24 which fix a heart valve stent to be implanted (not explicitly shown in FIG. 1).

The positioning stent 20 is configured as a self-expanding component. Due to the simple configuration of positioning stent 20, which essentially consists only of anchoring segment 21', docking segment 24' and shoulders 22, the positioning stent 20 exhibits extremely small dimensions when in its collapsed state. Thus, when inserting positioning stent 20, for example using a positioning stent catheter, the positioning stent 20 has very good maneuverability within aorta A. After positioning stent 20 has been inserted into aorta A, it is expanded, enabled, for example, by means of an external manipulation of the positioning stent catheter. The anchoring supports 21 of the expanded positioning stent 20 self-position into the pockets T of the patient's heart valve, whereby the alignment of the positioning stent 20 in the axial and horizontal direction is fixed relative the heart valve. So that the positioning stent 20 will expand independently, suitable pretensioning elements can be (optionally) provided. In the embodiment as shown, pretensioning elements are realized in the form of anchoring supports 21.

After positioning stent 20 is inserted into aorta A and positioned and fixed there as described above, a heart valve stent 10 (FIG. 2A) disposed with a prosthetic heart valve 11 at its proximal end is inserted into positioning stent 20. It expands subsequent to release and, in doing so, presses the old valve against the aorta wall, the positioning stent 20 respectively.

Figure 2A:
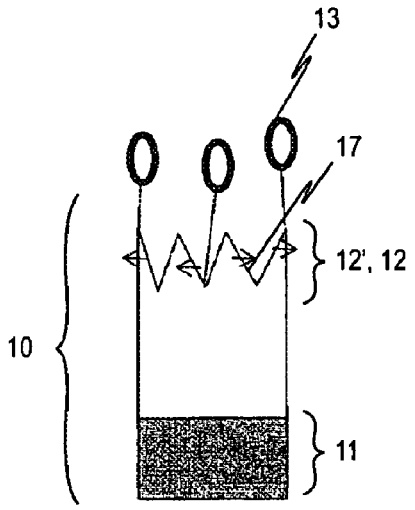
FIG. 2A: a preferred embodiment of a heart valve stent of the device according to the invention in the expanded state.

FIG. 2A shows a heart valve stent 10 in the expanded state. As depicted, the heart valve stent 10 has the prosthetic heart valve 11 at its proximal end and an anchoring segment 12' comprising at least one retaining element 12 at its distal end.

Figure 2B:
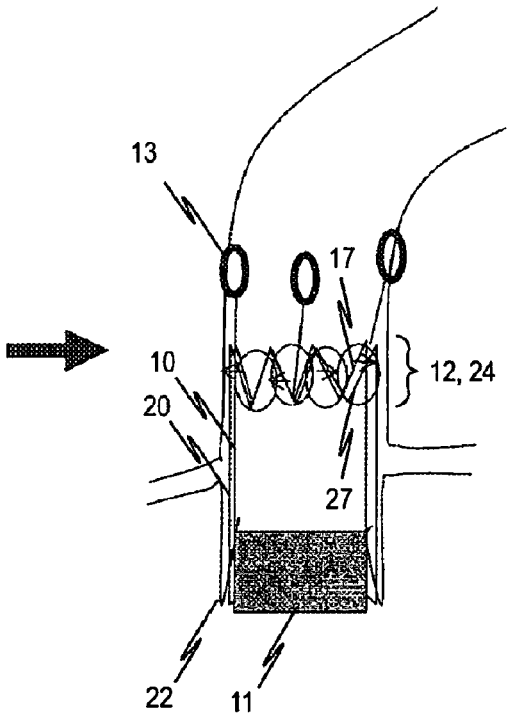
FIG. 2B: the heart valve stent of FIG. 2A in the implanted state.

FIG. 2B provides a representation of how the heart valve stent 10 is held in the already positioned and fixed positioning stent 20. The heart valve stent 10 is guided by guide elements 17, 27 in positioning stent 20 relative to rotation and axial position such that the new heart valve is optimally positioned. Thereafter, further releasing of the heart valve stent 10 introduces its anchoring segment 12' into docking segment 24' (FIG. 1) of the positioning stent 20. The anchoring segment 12' comprises retaining elements 12 which form a positive connection with the engaging elements 24 of the positioning stent 10 in order to position the prosthetic heart valve 11 in the position in the coronary artery as predefined by the positioning stent 20 and to hold same there by means of positioning stent 20.

Unlike conventional heart valve stents, the heart valve stent 10 of the present device does not have retaining clips to engage behind the old heart valve but rather engaging clips in the form of retaining elements 12 in the anchoring segment 12' of heart valve stent 10. These engaging clips interact with the engaging elements 24 disposed in the docking segment 24' of positioning stent 20. The advantage of this is that the heart valve stent 10 is commutably anchored in positioning stent 20. By means of its self-expanding induced by guide means 17, 27, heart valve stent 10 independently slides inside positioning stent 20 and cannot slide any further. The guide means 17, 27 are configured as elements tapering to the distal end of positioning stent 20 and/or heart valve stent 10. Due to the special design of engaging elements 23 of positioning stent 20 and the retaining elements 12 of heart valve stent 10 as clips formed in zigzag fashion (Z-clips), a finer angular positioning of the heart valve stent 10 can in particular ensue. Both the positioning stent 20 as well as the heart valve stent 10 can be configured of individual segments, whereby the individual segments can be rotated relative one another. This increases flexibility when inserting the two stents into the aorta. It is in particular possible to realize a finer angular positioning to heart valve stent 10. It is thus conceivable, for example, for the physician to alternatively insert a rotated prosthetic heart valve 11. The segmented configuration is also of advantage with respect to the collapsing of the heart valve stent and the positioning stent since the segmented stents in collapsed state can be housed compressed within a catheter.

Figure 3A:
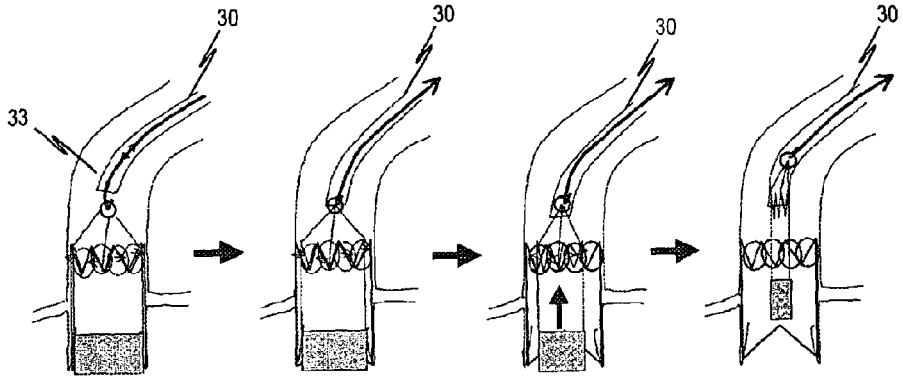
FIGS. 3A,B: one schematic representation each to illustrate the explantation process with a preferred embodiment of the heart valve stent.
Figure 3B:
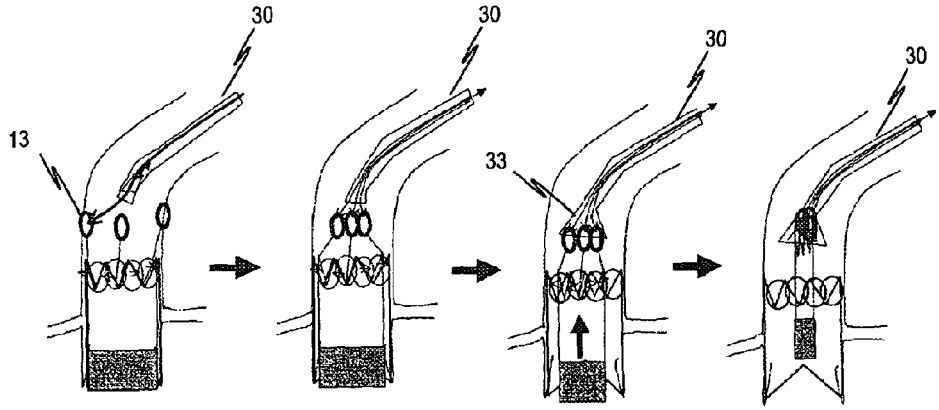
Figure 4:
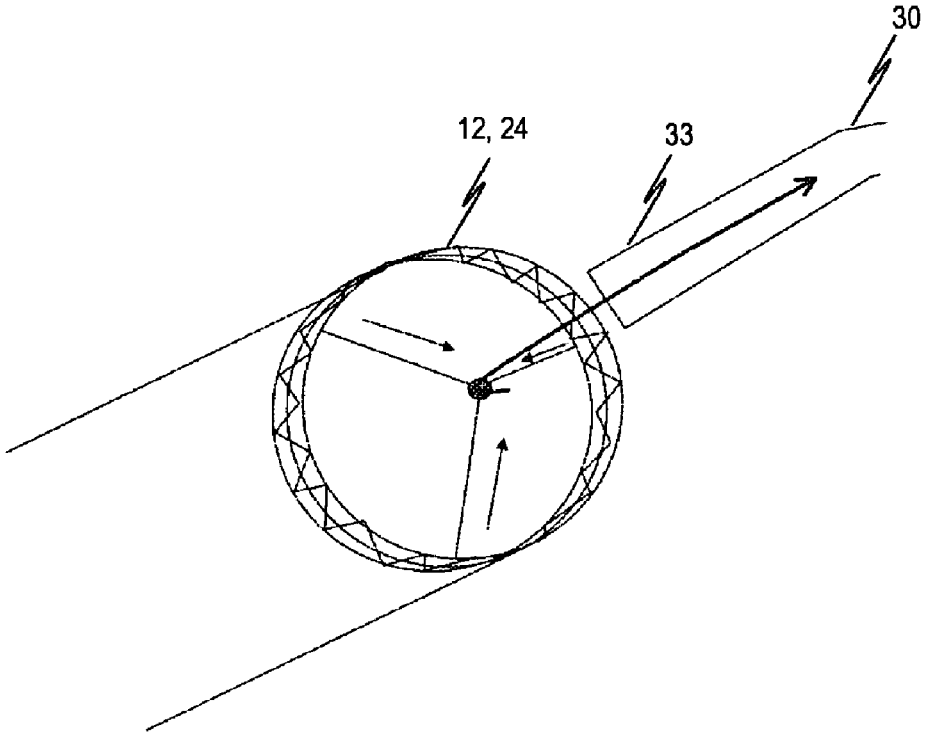
FIG. 4: a detailed representation of the explantation elements provided on the heart valve stent, the positioning stent respectively, as well as their mode of operation.

FIGS. 3A, 3B and 4 are schematic representations of how the heart valve stent 10 in the already positioned and implanted positioning stent 20 can be explanted. In the event of a valve dysfunction, the mechanically stable connection between the positioning stent 20 and the heart valve stent 10 as described above can be disengaged again by external manipulation. This can be realized, for example, by using a catheter 30 with a cartridge 33 affixed thereto to engage explantation elements 13. After retracting the explantation elements 13 into the variable funnel-shaped explantation catheter 30, the heart valve stent 10 is pulled into same and can thus be replaced with a new one. The positioning stent 20 remains as a marking and anchoring base for a new heart valve stent 10. Positioning stent 20 can, of course, also be explanted in a similar procedure.

The docking segment 24' of the positioning stent can comprise eyelets or nubs to which the explantation catheter 30 is to be affixed in order to effect such an explantation. Attaching to eyelets is possible via preferably three to six eyelets and three to six loops which are subsequently pulled out of the eyelets. The positioning stent 20 as well as the heart valve stent 10 is in particular completely reversibly withdrawable in the catheter, which enables the complete removal of the positioning stent and/or the heart valve stent.

The disengaging of the mechanically stable connection between positioning stent 20 and heart valve stent 10 by means of external manipulation, in the case of valve dysfunction for example, is possible when the previously implanted heart valve stent 10 exhibits a retrievable structure suitable for this purpose. This could consist of a plurality of connecting struts which project medially from the upper outer end of the stent into the vascular lumen and join there with an anchoring device (eyelet, hook, nub, etc.). Should this anchoring device now be grasped by the retrieval catheter wire of catheter 30, the distal portion of heart valve stent 10 can thus be compressed toward the lumen and drawn into a catheter tube 33. This then again provides the opportunity of using the positioning stent 20 which remains as a marking and anchoring base for a new heart valve stent 10.

The positioning stent 20 is made from a solid mesh (wire, polymer, etc.) or produced in a laser-cutting process. Applicable as suitable materials for the positioning stent are NiTi, high-grade steel or biocompatible plastics. For spatial orientation, x-ray markers can furthermore be disposed on positioning stent 20.

The invention claimed is:

1. A method of treating a native aortic valve, comprising:

positioning an expandable first stent adjacent the native aortic valve, the first stent having a first attachment element disposed adjacent a distal end of the first stent and at least one positioning element disposed adjacent a proximal end of the first stent, wherein the proximal end of the first stent is positioned closer to a patient's heart than the distal end of the first stent;

positioning the at least one positioning element behind a portion of a leaflet of the native valve, radially outward from the leaflet and radially inward from a portion of a vessel wall;

anchoring the first stent relative to the native aortic valve by expanding the first stent;

after expanding the first stent, positioning an expandable second stent radially within the first stent to connect the second stent to the first stent, the second stent having a second attachment element disposed adjacent a distal end of the second stent, wherein the proximal end of the second stent is positioned closer to the patient's heart than the distal end of the second stent; and compressing at least a portion of a leaflet of the native valve against a vessel wall such that the compressed portion of the leaflet is positioned radially inward from the at least one positioning element of the first stent and radially outward from a portion of the second stent component;

wherein the first and second attachment elements are complimentary to one another.

2. The method of claim 1, wherein the second stent includes a plurality of engagement elements configured to be selectively attached to a catheter.

3. The method of claim 1, further including:

disconnecting the second stent from the first stent; and positioning an expandable third stent radially within the first stent to connect the third stent to the first stent, the third stent having a third attachment element adjacent a distal end of the third stent;

wherein the first and third attachment elements are complimentary to one another.

4. The method of claim 1, further including:

positioning the at least one positioning element behind the portion of the leaflet before compressing a portion of the leaflet against the vessel wall.

* * * * *